(12) United States Patent
Grader

(10) Patent No.: US 11,971,369 B2
(45) Date of Patent: *Apr. 30, 2024

(54) METHODS AND SYSTEMS OF TESTING FORMATION SAMPLES USING A ROCK HYDROSTATIC COMPRESSION CHAMBER

(71) Applicant: Halliburton Energy Services, Inc.

(72) Inventor: Abraham S. Grader, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 300 days.

This patent is subject to a terminal disclaimer.

(21) Appl. No.: 17/305,153

(22) Filed: Jun. 30, 2021

(65) Prior Publication Data

US 2021/0325318 A1 Oct. 21, 2021

Related U.S. Application Data

(60) Continuation of application No. 16/354,569, filed on Mar. 15, 2019, now Pat. No. 11,085,887, which is a division of application No. 15/004,850, filed on Jan. 22, 2016, now Pat. No. 10,274,437.

(60) Provisional application No. 62/106,712, filed on Jan. 22, 2015.

(51) Int. Cl.
*G01N 23/046* (2018.01)
*A61K 9/51* (2006.01)

(52) U.S. Cl.
CPC .......... *G01N 23/046* (2013.01); *A61K 9/5123* (2013.01); *G01N 2223/309* (2013.01); *G01N 2223/311* (2013.01); *G01N 2223/616* (2013.01)

(58) Field of Classification Search
CPC .......... G01N 23/046; G01N 2223/311; G01N 2223/309; G01N 2223/616
See application file for complete search history.

(56) References Cited

U.S. PATENT DOCUMENTS

| | | | | |
|---|---|---|---|---|
| 4,688,238 A * | 8/1987 | Sprunt | ................. | G01N 23/046 378/62 |
| 4,884,455 A * | 12/1989 | Vinegar | ............... | G01N 23/046 73/152.11 |
| 5,226,310 A * | 7/1993 | Steiger | ..................... | G01N 3/10 73/794 |
| 11,085,887 B2 * | 8/2021 | Grader | ................. | G01N 23/046 |
| 2012/0281883 A1 * | 11/2012 | Hurley | ............... | G01N 21/6458 382/109 |

OTHER PUBLICATIONS

CN 110231457 A and English translation (2019). (Year: 2019).*

* cited by examiner

*Primary Examiner* — Chih-Cheng Kao
(74) *Attorney, Agent, or Firm* — K&L Gates LLP

(57) ABSTRACT

The disclosed embodiments include a rock sample inspection method. The method may include preparing a sample of formation rock by encapsulating the sample, inserting the sample into a vessel body as part of a test assembly, enclosing the sample within an low compressibility fluid, applying pressure to an interior of the vessel body by tightening a compression screw employing a piston acting on said low compressibility fluid, monitoring the pressure, conducting a test on the sample, and recording results of the test for further analysis.

20 Claims, 2 Drawing Sheets

METHODS AND SYSTEMS OF TESTING FORMATION SAMPLES USING A ROCK HYDROSTATIC COMPRESSION CHAMBER

CROSS-REFERENCE TO RELATED APPLICATIONS

The present application is a continuation of U.S. patent application Ser. No. 16/354,569 titled "Methods and Systems of Testing Formation Samples Using a Rock Hydrostatic Compression Chamber", filed Mar. 15, 2019, which is a Divisional of Ser. No. 15/004,850 titled "Methods and Systems of Testing Formation Samples Using a Rock Hydrostatic Compression Chamber", filed Jan. 22, 2016, patented as U.S. Pat. No. 10,274,437, issued on Apr. 30, 2019, which claims the benefit of U.S. Pat. App. 62/106,712 titled "Methods and Systems of Testing Formation Samples Using a Rock Compression Chamber", filed Jan. 22, 2015 by inventor Abraham Grader, which is incorporated by reference in its entirety.

BACKGROUND

Oilfield operators spend a great deal of time and resources when drilling and developing fields for petroleum products. It is essential for the operators to obtain detailed rock properties in order to optimize the production process. Some existing techniques for determining rock properties are not effective for many types of rocks.

BRIEF DESCRIPTION OF THE DRAWINGS

Accordingly, there are disclosed in the drawings and the following description methods and systems of testing formation samples using a hydrostatic rock compression chamber.

Figure 1:
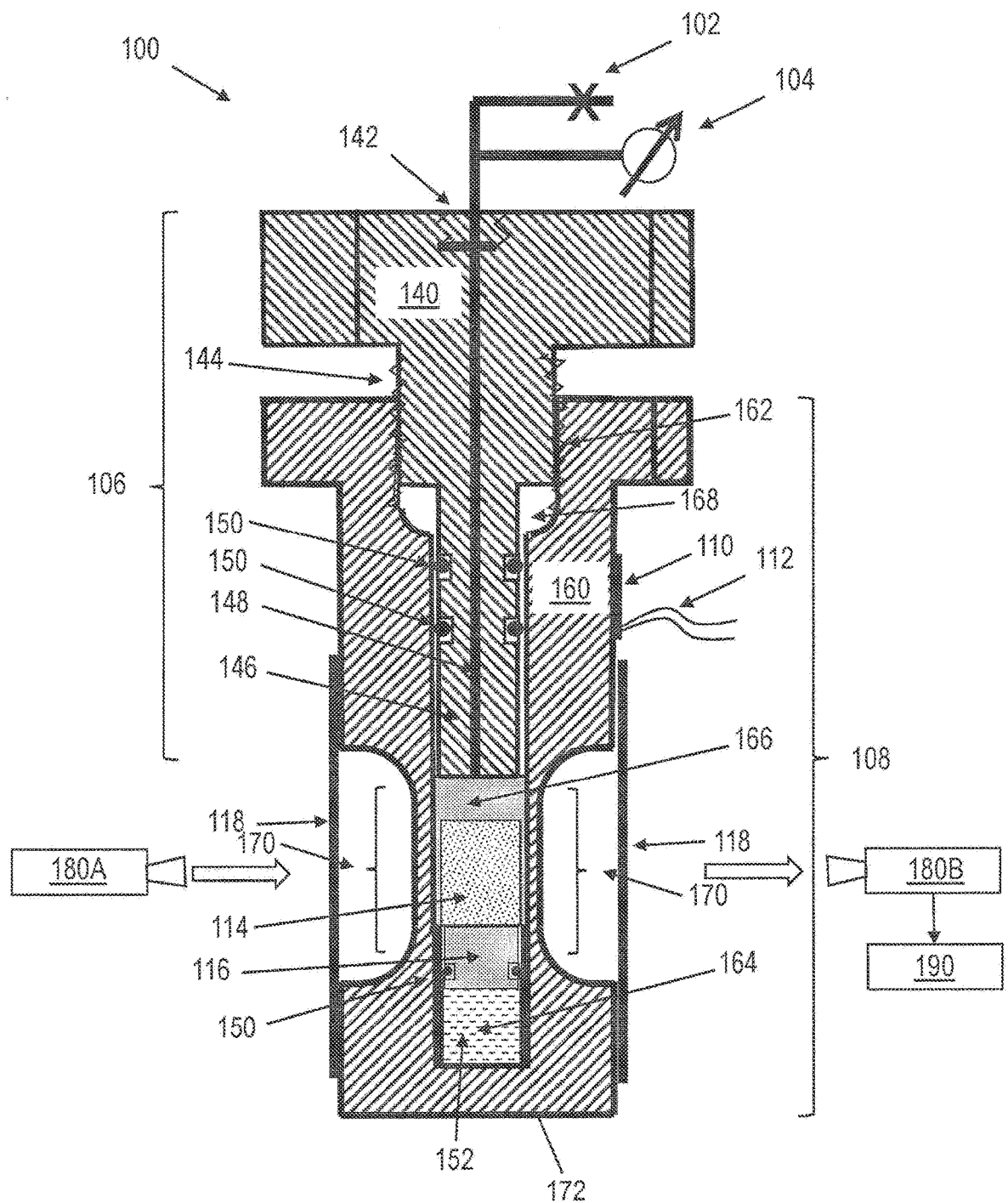
FIG. 1 is a cross-sectional diagram of an illustrative rock compression chamber in a micro-CT configuration.

It should be understood, however, that the specific embodiments given in the drawings and detailed description thereto do not limit the disclosure. On the contrary, they provide the foundation for one of ordinary skill to discern the alternative forms, equivalents, and modifications that are encompassed together with one or more of the given embodiments in the scope of the appended claims.

DETAILED DESCRIPTION

Disclosed herein are methods and systems for testing formation samples using a hydrostatic rock compression chamber (sample holder) to inspect a rock sample from an underground formation suspected of containing oil and gas products but not limited to oil and gas. In this disclosure, the sample may be (but not limited to) a cylinder of formation rock that is suspected to contain fluids in the form of water, oil, or gas in unknown concentrations. The sample may be imaged using X-ray CT prior to compression to determine its interior solid and pore structure from which various properties are determined. Applying pressure to the rock sample is essential to place the sample under simulated conditions downhole and to witness and record the elastic and plastic recovery of the rock under simulated downhole stress conditions. The images of the rock under stress yield, through analysis, the rock properties and their dependency on stress.

Accordingly, FIG. 1 shows an illustrative rock compression chamber test assembly 100 (test assembly including the sample holder) which is comprised of a relief valve 102, a pressure gauge 104, a compression screw assembly 106, a vessel body assembly 108, an optional strain gauge 110 with a set of strain gauge wires 112, a rock sample assembly 114, a bottom plug 116, and an optional plastic enforcer tube 118. The strain gauge 110 may be connected to a monitoring device (not shown) by the strain gauge wires 112 to monitor and record pressures felt by the test assembly 100. A test measurement device, such as a micro-CT scanner, comprised of a radiation source 180A, a detector 180B, along with a controller and measurement recording device 190 is used to irradiate the vessel body assembly 108 (and the sample enclosed within) with radiation and record the resultant signals. The optional plastic enforcer tube 118 may be used to add structural strength to the vessel body assembly 108, specifically around a thin-walled region 170. The plastic enforcer tube 118 is optional, but when used may prevent bending when the thin-walled region 170 is of such length that the thinness results in a low structural strength despite being sufficient to maintain the design pressure levels internally.

The vessel body assembly 108 is comprised of a vessel body 160, a set of threads 162, and an interior chamber 168 including an air chamber 164 and a hydraulic fluid chamber 166. The interior chamber 168 extends most of the length of the interior of the vessel body 160 and includes the air chamber 164. The vessel body assembly 108 is made of titanium alloy or other similar material that has high strength while having as little mass as possible. The use of titanium or similar materials is preferred to minimize the losses associated with interactions with the radiation(s) emitted by the source 180A. In one embodiment, the interior chamber 168 is cylindrical with an inner diameter of 7 mm, with the air chamber 164 cylindrical with an inner diameter of 6 mm Other embodiments have interior diameters of 1-5 mm Typical thickness of the wall in the thin-walled region is 1 mm of titanium alloy but may be as thin as 0.5 mm in other embodiments, based on the design pressure. A typical design pressure is 4000 psig with operational pressures up to the 2500 psig range. All embodiments include appropriate safety factors for any given component.

Continuing with the vessel body assembly 108, the bottom plug 116 is placed into the interior chamber 168. The bottom plug 116 uses at least one O-ring 150 to create a fluid-tight seal to define and isolate the air chamber 164. The vessel body 160 also includes the thin-walled region 170 to minimize the amount of matter the radiation has to traverse when emitted from the source 180A to the detector 180B.

The compression screw assembly 106 is comprised of a compression screw body 140 (stainless steel 316 or similar alloy for material compatibility with the vessel body 160), a conduit connector 142, a set of threads 144 for mechanical coupling to the threads 162 present on the vessel body 160, a piston arm 146, a fluid conduit 148 located within the piston arm 146, and at least one O-ring 150 to maintain pressure and establish fluid isolation when the test assembly 100 is in use. The compression screw assembly 106 may be made of steel or other material that can withstand high pressures without deforming Reference marks (not shown) may be placed on the outside of the compression screw assembly 106 to allow an operator to monitor the position of the compression screw assembly 106 in reference to the vessel body assembly 108. The conduit connector 142 may either be used to seal off the fluid conduit 148 or to attach additional test devices such as the relief valve 102 or the pressure gauge 104 as required. Once screwed into the vessel body assembly 108, the compression screw assembly 106 may be tightened using the threads 144 against the vessel body 160 threads 162. In this way, the piston arm 146 of the compression screw assembly 106 reduces the volume of the interior chamber 168 of the vessel body assembly 108. As a consequence, as the volume of the interior chamber 168 is reduced, the pressure in the interior chamber 168 is increased. Pressure in the interior chamber 168 is thus controlled by tightening or loosening the compression screw assembly 106 in relation to the vessel body assembly 108. Pressure felt at the end of the piston arm 146 may be monitored by attaching the pressure gauge 104 to the fluid conduit 148.

The hydraulic fluid is preferably only slightly compressible (less than 1% at 1000-4000 psig at room temperature is standard) so that the compression of the air chamber allows for ease of setting the pressure inside the interior chamber 168. In an embodiment without the air chamber 164, the hydraulic fluid is preferably more compressible than standard as standard hydraulic fluid acted on by a piston makes setting a precise pressure level difficult.

To conduct an analysis, the sample is prepared. A sample of formation rock of interest (not shown) may be prepared by cutting a sample of rock into a cylinder shape approximately 5 mm long and 5 mm in diameter. The rock sample is then preferably encapsulated by a covering that is impermeable to fluids such as water and petroleum components. The covering may be one of heat shrink material, waterproof paint, plastic wrap, or any of a number of other materials. The purpose of the covering separate the rock from the compressing fluid in the chamber 166, so that net confining stress is transmitted to the rock sample assembly 114. The rock sample assembly 114 is thus comprised of a portion of formation rock cut into a cylinder shape and covered in a fluid-tight covering. In other embodiments, the rock sample assembly includes one or two anvils (see FIG. 2) either below or both above and below the rock sample itself. Preferably, the anvils are made of aluminum or other material similar in composition to the rock sample so as not to interfere with the sample testing.

The threads 162 are shown internal, but other embodiments may be external, so long as the compression screw assembly 106 has matching threads and the piston engages the hydraulic fluid in the hydraulic fluid chamber 116. Note that the base 172 may include screws or dowels (not shown) or holes to accept screws or dowels to aid in placement and in securing the sample holder in the micro-CT scanner.

Figure 2:
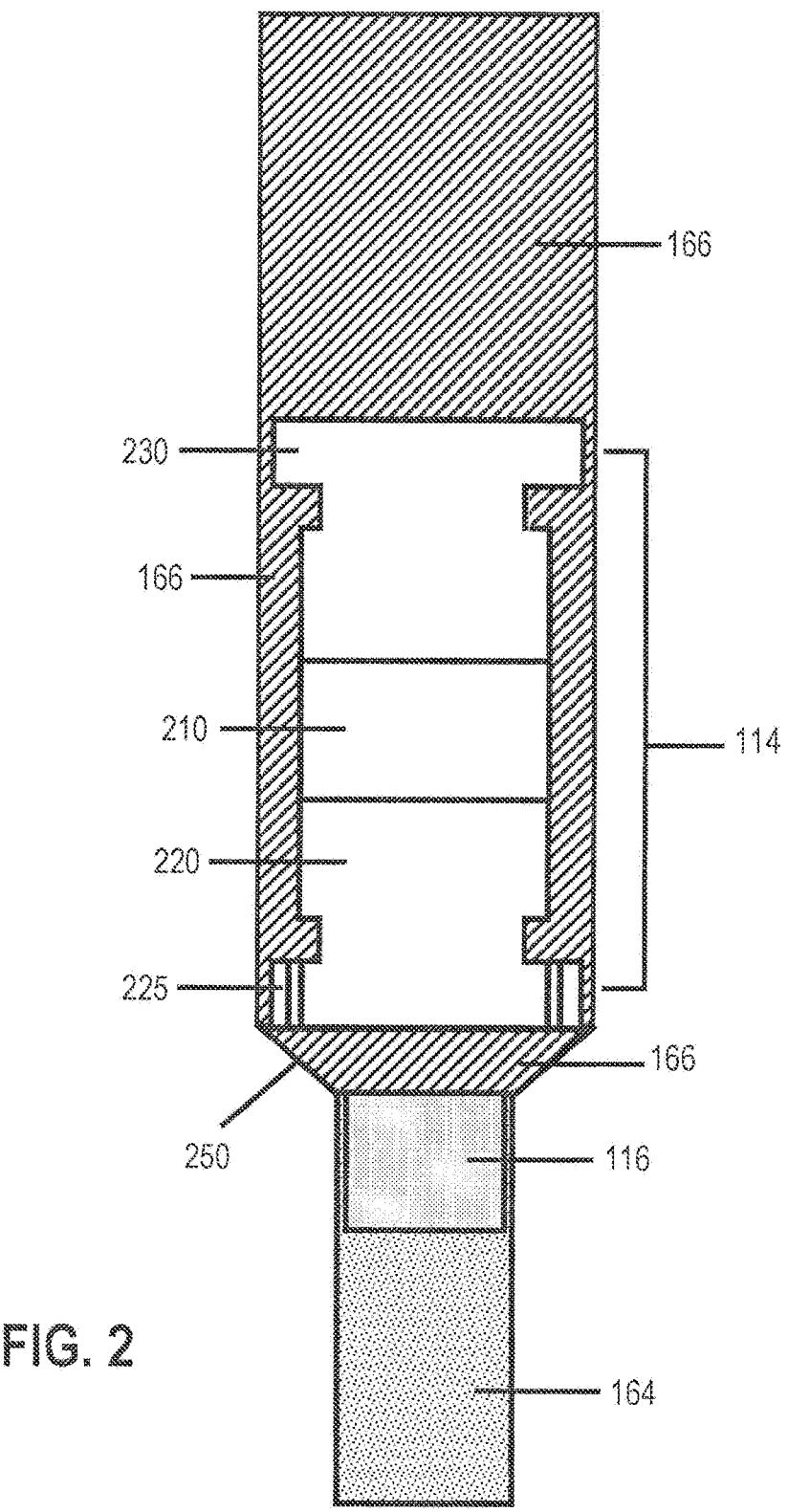
FIG. 2 is a line drawing of a preferred embodiment of the sample positioning in the illustrative rock compression chamber.

Turning now to FIG. 2, the line drawing of a preferred embodiment of the sample positioning in the illustrative rock compression chamber is shown. In this embodiment, the rock sample assembly 114 includes the rock sample 210 between a position-locating anvil 220 below the rock sample 210 and an upper anvil 230 above the rock sample. The position-locating anvil 220 rests on shoulders 250 that act as fixed reference stops 250. The user knows that the position-locating anvil 220 will rest on the fixed reference stops 250 and that the bottom of the sample 210 meets the top of the position-locating anvil 220. So the location of the bottom of the sample 210 is always known and fixed. The upper anvil 230 is optional.

Using the upper anvil 230 allows for encapsulation to occur part of all of the upper anvil 230, the sample 210, and all or part of the position-locating anvil 220. The position-locating anvil 220 preferably has passages 225 for the hydraulic fluid to flow below the position-locating anvil 220 and contact the bottom plug 116. The bottom plug 116 is sized to fit snugly against the inner wall so that a gas bubble of varying size is maintained in the air chamber 164. In practice, the bottom plug 116 may use the O-ring 150 shown in FIG. 1 or be properly sized for an inside wall sufficiently uniform in geometry that capillary forces prevent the hydraulic fluid from invading the air chamber 164. The shoulder 250 may be completely perpendicular to the inner wall or have a slope. In another embodiment, the stop or stops 250 may be part of an insert that bottom plug 116 moves along or inside instead of being integral with the vessel body 160, so long as the air chamber 164 is not invaded by the hydraulic fluid to prevent control of the pressure within the interior chamber 168 within the hydraulic fluid chamber 166.

To prepare the test assembly 100 for testing, the vessel body assembly 108 is cleaned of all contaminants. The bottom plug 116 is inserted into the interior chamber 168. It is important to not allow the bottom plug 116 to travel all of the way to the bottom of the vessel body assembly 108 as the air chamber 164 plays an important part in the test assembly 100. Then, the rock sample assembly 114 is placed in the interior chamber 168, resting above the bottom plug 116. Hydraulic fluid within hydraulic fluid chamber 166, surrounding the encapsulated sample assembly 114, is then injected into the interior chamber 168 above the rock sample assembly 114, bottom plug 116, and the air chamber 164 filling the remainder of the interior chamber 168 with fluid to form the hydraulic fluid chamber 166 around the rock sample assembly 114. Thus assembled, the interior chamber 168 contains the rock sample assembly 114 above the air chamber 164 and surrounded by hydraulic fluid in the hydraulic fluid chamber 166. Finally, the compression screw assembly 106 is threaded into the vessel body assembly 108.

To conduct an analysis of the rock sample assembly 114, the compression screw assembly 106 is tightened in relation to the vessel body assembly 108 while the pressure in the interior chamber 168 is monitored by the pressure gauge 104 or the strain gauge 110. It is desirable to place the rock sample assembly 114 under pressure while conducting the test as it is desirable to simulate actual downhole pressures to witness the characteristics of the rock sample assembly 114 under estimated downhole conditions. Once the desired pressure is reached, the analysis may begin using a CT scan or other measurement scanning techniques using the test measurement device. For a CT scan, the radiation are typically X rays, while the detector is typically a scintillator array or even a single crystal. The controller and measurement recording device 190 is typically a computer system with motor controllers and switches. In an illustrative embodiment, the X rays are created from electrons accelerated with voltages ranging from 20-100 kV with power output about 10 W.

In another embodiment, there may be a bottom threaded hole with a screw plug (not shown) at the base 172 of the vessel body 160. Note that the preferred placement of radiation source 180A and detector 180B is as close as practical to the sample 210. In practice, those locations, when the plastic enforcer tube 118 is not present, are where the plastic enforcer tube 118 is shown in FIG. 1. When the plastic enforcer tube 118 is present, those locations are approximately 1 mm from the plastic enforcer tube 118. Those of skill in the art will appreciate the location being close to but distant enough to avoid complications with being right at the surface of the plastic enforcer tube 118. Note that substantially incompressible herein means anything less than 0.2% at operating pressure. All embodiments or illustrative examples not given as alternatives to each other are combined with each other as additional disclosed embodiments.

What is claimed is:

1. A rock sample inspection method, comprising:
   preparing a sample of formation rock by encapsulating the sample;
   inserting the sample into a vessel body assembly comprising a vessel body and an interior chamber;
   enclosing the sample within a fixed volume of a low compressibility fluid in the interior chamber;
   increasing a fluidic pressure applied to the sample by the fixed volume of the low compressibility fluid in the interior chamber by adjusting the volume of the interior chamber;
   monitoring the fluidic pressure;
   conducting a measurement scanning test on the sample; and
   recording results of the measurement scanning test.

2. The method of claim 1, further comprising, prior to conducting the measurement scanning test on the sample, allowing the vessel body and fluid to reach temperature equilibrium.

3. The method of claim 1, further comprising, prior to said increasing fluidic pressure to the interior chamber, conducting the measurement scanning test on the sample without additional increased fluidic pressure.

4. The method of claim 1, wherein preparing the sample of formation rock comprises cutting the sample into a shape.

5. The method of claim 1, further comprising compressing a compressible fluid within an air chamber of the vessel body when the volume is adjusted.

6. The method of claim 1, further comprising encapsulating the sample in a covering that is impermeable to the low compressibility fluid.

7. The method of claim 1, further comprising depressurizing the interior chamber and repressurizing the interior chamber to test elastic recovery of the sample.

8. The method of claim 1, further comprising cleaning the vessel body.

9. The method of claim 1, wherein the low compressibility fluid compresses less than 0.2 percent at the pressure.

10. The method of claim 1, wherein the measurement scanning test comprises a micro-CT scanning test.

11. A method of inspecting a rock sample, comprising:
    inserting the rock sample into a hydraulic fluid chamber of a vessel body;
    injecting hydraulic fluid into the hydraulic fluid chamber;
    increasing a fluidic pressure applied to the rock sample by a fixed volume of the hydraulic fluid in the hydraulic fluid chamber by adjusting the volume of the hydraulic fluid chamber; and
    conducting a measurement scanning test on the sample.

12. The method of claim 11, further comprising allowing the vessel body and hydraulic fluid to reach temperature equilibrium prior to conducting the measurement scanning test on the sample.

13. The method of claim 11, further comprising conducting the measurement scanning test on the sample prior to increasing the fluidic pressure in the hydraulic fluid chamber.

14. The method of claim 11, further comprising monitoring the fluidic pressure in the hydraulic fluid chamber of the vessel body during the measurement scanning test.

15. The method of claim 11, further comprising compressing a compressible fluid within an air chamber of the vessel body when the volume of the hydraulic fluid chamber is adjusted.

16. The method of claim 11, wherein the measurement scanning test comprises a CT scan.

17. The method of claim 11, further comprising encapsulating the sample in a covering that is impermeable to the hydraulic fluid.

18. The method of claim 11, further comprising decreasing the fluidic pressure in the hydraulic fluid chamber and then conducting a second test.

19. The method of claim 18, further comprising decreasing the fluidic pressure in the hydraulic fluid chamber and then conducting a third test.

20. The method of claim 11, wherein conducting a measurement scanning test comprises conducting a micro-CT scanning test.

* * * * *